(12) United States Patent
Theiste et al.

(10) Patent No.: US 10,971,718 B2
(45) Date of Patent: *Apr. 6, 2021

(54) ELECTROCHEMICAL ENERGY STORAGE DEVICES

(71) Applicant: Gentex Corporation, Zeeland, MI (US)

(72) Inventors: David A Theiste, Zeeland, MI (US); Leroy J. Kloeppner, Zeeland, MI (US); Sue F. Franz, Zeeland, MI (US); Punam Giri, Holland, MI (US); Rongguang Lin, Holland, MI (US)

(73) Assignee: GENTEX CORPORATION, Zeeland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/595,056

(22) Filed: Oct. 7, 2019

(65) Prior Publication Data

US 2020/0050070 A1 Feb. 13, 2020

Related U.S. Application Data

(60) Continuation of application No. 15/853,420, filed on Dec. 22, 2017, now Pat. No. 10,481,456, which is a
(Continued)

(51) Int. Cl.
| | | |
|---|---|---|
| *H01M 4/137* | (2010.01) | |
| *H01M 4/60* | (2006.01) | |
| *H01M 4/66* | (2006.01) | |
| *H01M 10/05* | (2010.01) | |
| *H01M 6/18* | (2006.01) | |
| *H01M 4/36* | (2006.01) | |
| *H01G 11/04* | (2013.01) | |
| *H01G 9/02* | (2006.01) | |
| *H01G 9/035* | (2006.01) | |
| *H01G 9/042* | (2006.01) | |
| *H01G 9/145* | (2006.01) | |
| *H01G 11/48* | (2013.01) | |
| *H01M 10/0567* | (2010.01) | |

(Continued)

(52) U.S. Cl.
CPC .......... *H01M 4/137* (2013.01); *G02F 1/1506* (2013.01); *G02F 1/1525* (2013.01); *H01G 9/02* (2013.01); *H01G 9/035* (2013.01); *H01G 9/0425* (2013.01); *H01G 9/145* (2013.01); *H01G 11/04* (2013.01); *H01G 11/48* (2013.01); *H01M 4/366* (2013.01); *H01M 4/606* (2013.01); *H01M 4/608* (2013.01); *H01M 4/66* (2013.01); *H01M 6/18* (2013.01); *H01M 10/05* (2013.01); *H01M 10/0567* (2013.01); *C07D 241/48* (2013.01); *C07D 279/28* (2013.01); *G02F 1/1503* (2013.01); *G02F 1/15165* (2019.01); *G02F 2001/1518* (2019.01); *G02F 2001/15145* (2019.01); *H01G 11/52* (2013.01); *H01G 11/62* (2013.01); *H01M 10/0568* (2013.01); *H01M 10/0569* (2013.01); *H01M 2004/027* (2013.01); *H01M 2004/028* (2013.01); *Y02E 60/13* (2013.01)

(58) Field of Classification Search
CPC ... C07D 241/18; C07D 279/28; G02F 1/1503; G02F 1/1506; G02F 1/15165; G02F 1/1525; G02F 2001/15145; G02F 2001/1518; H01G 9/02; H01G 9/035; H01G 9/0425; H01G 9/145; H01G 11/04; H01G 11/48; H01G 11/52; H01G 11/62; H01M 4/137; H01M 4/366; H01M 4/66; H01M 4/606; H01M 4/608; H01M 6/18; H01M 10/05; H01M 10/0567; H01M 10/0568; H01M 10/0569; H01M 2004/027; H01M 2004/028; Y02E 60/10; Y02E 60/13

See application file for complete search history.

(56) References Cited

U.S. PATENT DOCUMENTS

| | | |
|---|---|---|
| 3,951,687 A | 4/1976 | Takamura et al. |
| 4,902,108 A | 2/1990 | Byker |
| | (Continued) | |

FOREIGN PATENT DOCUMENTS

| | | |
|---|---|---|
| CN | 101069124 A | 11/2007 |
| WO | WO-2008/146674 A1 | 12/2008 |

OTHER PUBLICATIONS

Barbosa et al, "The receptor-dependent LQTA-QSAR: application to a set of trypanothione reductase inhibitors", Journal of Computer-Aided Molecular Design, Kluwer Academic Publishers, DO, (Sep. 13, 2012), vol. 26, No. 9, doi:10.1007/S10822-012-9598-2, ISSN 1573-4951, pp. 1055-1065.

(Continued)

*Primary Examiner* — Anca Eoff
(74) *Attorney, Agent, or Firm* — Foley & Lardner LLP; Bradley D. Johnson

(57) ABSTRACT

An energy storage device includes a cathodic material in an activated state; and an anodic material in an activated state; wherein: the cathodic material is covalently attached to, or confined within, a first polymer matrix, the first polymer matrix is configured to prevent or minimize substantial diffusion of the cathodic material in the activated state; and the anodic material is a phenazine, a phenothiazine, a triphenodithiazine, a carbazole, a indolocarbazole, a biscarbazole, or a ferrocene covalently attached to, or confined within, a second polymer matrix, the second polymer matrix is configured to prevent or minimize substantial diffusion of the anodic material in the activated state.

18 Claims, 1 Drawing Sheet

Related U.S. Application Data division of application No. 14/721,934, filed on May 26, 2015, now Pat. No. 9,964,828.

(60) Provisional application No. 62/057,811, filed on Sep. 30, 2014, provisional application No. 62/003,335, filed on May 27, 2014.

(51) Int. Cl.
| | |
|---|---|
| *H01M 10/0568* | (2010.01) |
| *H01M 10/0569* | (2010.01) |
| *H01G 11/62* | (2013.01) |
| *H01M 4/02* | (2006.01) |
| *G02F 1/1506* | (2019.01) |
| *G02F 1/1523* | (2019.01) |
| *G02F 1/1503* | (2019.01) |
| *G02F 1/1516* | (2019.01) |
| *G02F 1/1514* | (2019.01) |
| *C07D 241/48* | (2006.01) |
| *C07D 279/28* | (2006.01) |
| *H01G 11/52* | (2013.01) |

(56) References Cited

U.S. PATENT DOCUMENTS

| | | | |
|---|---|---|---|
| 5,294,376 A | 3/1994 | Byker | |
| 5,840,443 A * | 11/1998 | Gregg | H01M 4/608 |
| | | | 429/212 |
| 5,940,201 A | 8/1999 | Ash et al. | |
| 5,998,617 A | 12/1999 | Srinivasa et al. | |
| 6,188,505 B1 | 2/2001 | Lomprey et al. | |
| 6,193,912 B1 | 2/2001 | Thieste et al. | |
| 6,635,194 B2 | 10/2003 | Kloeppner et al. | |
| 6,710,906 B2 | 3/2004 | Guarr et al. | |
| 7,046,418 B2 | 5/2006 | Lin et al. | |
| 8,228,590 B2 | 7/2012 | Baumann et al. | |
| 10,481,456 B2 * | 11/2019 | Theiste | G02F 1/1506 |
| 2002/0141032 A1 | 10/2002 | Guarr et al. | |
| 2003/0165000 A1 | 9/2003 | Roberts et al. | |
| 2005/0164075 A1 * | 7/2005 | Kumamoto | H01M 8/2455 |
| | | | 429/50 |
| 2006/0103911 A1 | 5/2006 | Baumann et al. | |
| 2008/0186564 A1 | 8/2008 | Noh et al. | |
| 2008/0310007 A1 | 12/2008 | Agrawal et al. | |
| 2010/0208325 A1 * | 8/2010 | Piroux | C09K 9/02 |
| | | | 359/268 |
| 2012/0041163 A1 * | 2/2012 | Tang | C07F 17/02 |
| | | | 526/241 |
| 2012/0176658 A1 | 7/2012 | Das et al. | |
| 2015/0333331 A1 * | 11/2015 | Johnson | H01M 4/608 |
| | | | 429/213 |
| 2019/0048159 A1 | 2/2019 | Erno et al. | |

OTHER PUBLICATIONS

Basonat HI grades, BASF Technical Information, Mar. 2005 (3 pages).
Communication issued for EP 15799535.8, dated Dec. 18, 2018 (7 pages).
Extended European Search Report issued in EP 15799535.8 dated Mar. 1, 2018 (13 pages).
Final Rejection Office Action on U.S. Appl. No. 14/721,934 dated Jun. 22, 2017 (10 pages).
International Search Report and Written Opinion on International Application No. PCT/US2015/032459 dated Sep. 10, 2015 (11 pages).
Non-Final Office Action on U.S. Appl. No. 15/853,420 dated May 3, 2019 (10 pages).
Non-Final Rejection Office Action on U.S. Appl. No. 14/721,934 dated Mar. 1, 2017 (9 pages).
Notice of Allowance on U.S. Appl. No. 14/721,934 dated Jan. 2, 2018 (7 pages).
Notice of Allowance on U.S. Appl. No. 15/853,420 dated Jul. 18, 2019 (8 pages).
Office Action on CN Application No. 201580040323.6 dated Apr. 8, 2019, (14 pages).
Extended European Search Report on EP Application No. 19186800.9 dated Sep. 19, 2020 (10 pages).
Foreign Office Action on CN Patent Application No. 201580040323.6 dated Jan. 22, 2020 (with English translation) (8 pages).
Foreign Office Action on EP Patent Application No. 19186800.9 dated Nov. 2, 2020 (6 pages).
Fujinami T., et al., "Polymer electrolyte bilayer films with photorechargeable battery characteristics," Solid State Ionics, North Holland Pub. Co. Amsterdam, NL, 92(3):165-169 (1996).

* cited by examiner

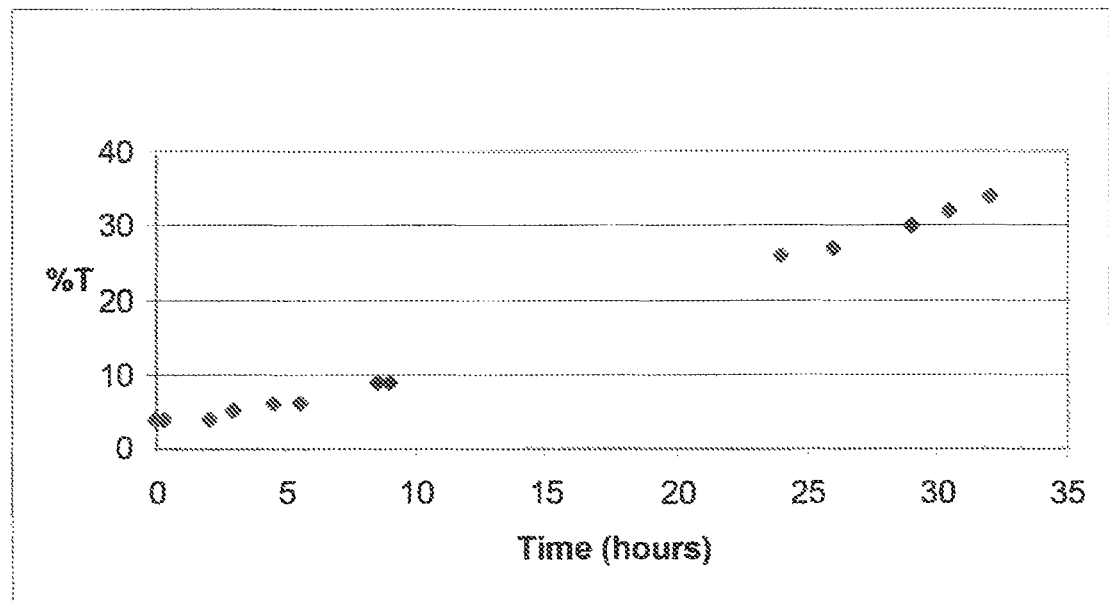

ELECTROCHEMICAL ENERGY STORAGE DEVICES

CROSS-REFERENCE TO RELATED APPLICATIONS

This continuation application claims the benefit of U.S. patent application Ser. No. 15/853,420, filed Dec. 22, 2017, which claims priority to Ser. No. 14/721,934, filed May 26, 2015 (now U.S. Pat. No. 9,964,828, issued May 8, 2018), which claims U.S. Provisional Patent Application Nos. 62/003,335, filed on May 27, 2014, and 62/057,811, filed on Sep. 30, 2014, the entire disclosures of which are incorporated herein by reference for any and all purposes.

FIELD

The present technology is generally related to electrochromic devices. More particularly, it is related to electrochromic devices having a persistent color memory and can provide a current during clearing for a substantial time period after being charged.

SUMMARY

In one aspect, an energy storage device includes a cathodic material in an activated state; and an anodic material in an activated state; wherein: the cathodic material is a viologen covalently attached to, or confined within, a first polymer matrix, the first polymer matrix configured to prevent or minimize substantial diffusion of the cathodic material in the activated state; and the anodic material is a phenazine, a phenothiazine, a triphenodithiazine, a carbazole, a indolocarbazole, a biscarbazole, or a ferrocene covalently attached to, or confined within, a second polymer matrix, the second polymer matrix configured to prevent or minimize substantial diffusion of the anodic material in the activated state. The activated cathodic and anodic materials may be separated by an electrolyte solution or gel layer in order to substantially minimize electron transfer between activated states. Illustrative energy storage devices include batteries, capacitors, supercapacitors, and the like.

In one aspect, an energy storage device includes a first cell including an anodic material; a second cell including a cathodic material; a porous separator isolating the first cell from the second cell; wherein: the anodic material is a phenazine, a phenothiazine, a triphenodithiazine, a carbazole, a indolocarbazole, a biscarbazole, or a ferrocene; and the cathodic material is a viologen. In addition, the anodic and cathodic materials in their activated states are prevented or hindered from passage through the porous separator to stop or minimize electron transfer and deactivation of the activated states (i.e. "self-erase").

BRIEF DESCRIPTION OF FIGURES

The FIGURE shows the percentage of transmission as a function of time at open circuit for a device according to Example 15.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6- disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, $CH-CH=CH_2$, $C=CH_2$, or $C=CHCH_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, "darkening time" is defined as the time needed to reach 90% of the total transmission change from highest to lowest transmission values as measured on an electrochromic device.

Typical solution-phase electrochromic devices contain at least one anodic (oxidizable) material, at least one cathodic (reducible) material, and a solvent. Upon charging, i.e. activation, of the typical solution-phase devices to produce a colored state, internal diffusion processes lead to continual self-erasing that results in de-coloration upon removal of the charging source. It has now been found that sequestration of an anodic material in a polymer matrix and a cathodic material in a polymer matrix, or a chambered isolation of the materials in an electrochromic device, results in electrochromic devices that are configured to maintain the charged, i.e. activated, state for prolonged periods of time in comparison to typical solution-phase electrochromic devices. The sequestration in separate polymer matrices or in isolated chambers prevents the activated anodic and cathodic materials from readily undergoing charge transfer processes leading to de-coloration. Further, because the activated species are maintained upon removing of the charging source, the activated electrochromic devices are also batteries. The cathodic and anodic compounds may be merely sequestered within the polymer matrix and separated from one another. Alternatively, the cathodic, the anodic, or the cathodic and the anodic compounds may be polymerized into the polymer matrix through functionalization of the anodic or cathodic materials.

The electrochromic devices described herein include at least one chamber defined by a first substrate having a first conductive surface, a second substrate having a second conductive surface, and a sealing member joining the first substrate to the second substrate with the first and second conductive surfaces contacting the sealing member. For the surface confinement of the anodic and cathodic materials, the anodic material may be sequestered on the first conductive surface and the cathodic material may be sequestered on the second conductive surface. Within the chamber is disposed an electrolyte between the anodic and cathodic layers. The first and second substrates may be off-set to one another to allow for electric contact to be made with the first and second conductive surfaces, as is well established for other solution phase electrochromic devices.

For the chambered isolation devices, at least one chamber of the electrochromic device is further divided into a first chamber and a second chamber by a separator positioned between the first and second substrates. The first chamber is defined by the first substrate, sealing member and a first surface of the separator. The second chamber is defined the second substrate, sealing member, and a second surface of the separator, the second surface being located opposite to the first surface. The sealing member may also be divided as a first sealing member joining the first substrate to the first surface of the separator and a second sealing member joining the second substrate to the second surface of the separator. The separator allows the movement of electrolyte between the first and second chamber, but prevents or substantially minimizes the passage of activated cathodic and anodic materials between the same two chambers.

In one aspect, an energy storage device is provided. The energy storage device may include a cathodic material in an activated state, and an anodic material in an activated state. The cathodic material may be a viologen covalently attached to, or confined within, a first polymer matrix, the first polymer matrix configured to prevent or minimize substantial diffusion of the cathodic material in the activated state. As noted above, the viologen may be sequestered within the polymer matrix by being physically trapped within, or the viologen may be functionalized such that it is amenable to being polymerized or reacted with the polymer to be covalently bonded to the polymer. The energy storage device may be a battery, a capacitor, or a supercapacitor.

In another aspect, an energy storage device is provided, the device including a first cell including an anodic material; a second cell including a cathodic material; and a porous separator isolating the first cell from the second cell. The separator includes an ion exchange membrane or a size-exclusion membrane. The energy storage device may be a battery, a capacitor, or a supercapacitor.

In some embodiments the separator is a membrane. Illustrative membranes may include paper membranes, polymer membranes, ceramic membranes, glass membranes, composite membranes, ion-selective membranes, homogeneously dense membranes or porous size-exclusion membranes. Illustrative materials that may be used for membranes are: cellulose acetate; cellulose esters; nitrocellulose; polyvinylidenefluorides; polysulfones; polyacrylonitriles; polyamides; polypropylene; polyacrylates; polymethacrylates; polyethylene; polystyrenes; polyvinylchloride; negatively charged materials such as, but not limited to, sulfonated tetrafluoroethylene polymers and copolymers or Nafion®; positively charged materials such as, but not limited to, ammoniated polystyrene copolymers such as AMI-7001 from Membranes International Inc.; poly(vinyl pyridinium) co-polymers; poly(vinyl imidazolium) co-polymers; ceramic materials such as, but not limited to, aluminum oxide, titanium oxide, zirconium oxide, silicon oxide; and porous carbon; or a combination of any two or more such materials.

In another aspect, an electrochromic device includes a cathodic material covalently attached to, or confined within, a first polymer matrix; and an anodic compound covalently attached to, or confined within, a second polymer matrix. The electrochromic device exhibits a high transmission state at short circuit and a low transmission state upon application of an electric potential, where the high transmission state is at least 5 times greater than the low transmission state; and the electrochromic device is configured to maintain a transmission percentage within 20% of the low transmission state for at least 5 hours at open circuit after application of a potential sufficient to reach to the low transmissions state. The low transmission state may range from about 0.001% to about 30%. The high transmission state range from about 50% to about 95%. In some embodiments, after 4000 cycles from the high transmission state to the low transmission state, a high transmission value does not vary by more than 5% from an initial high transmission value. As used herein the initial high transmission value is the state of the device prior to the application of an electric potential after device fabrication. In some embodiments, after 4000 cycles from high transmission to low transmission, the low transmission value does not vary by more than 5% from an initial low transmission value. As used herein, the initial low transmission value is the low transmission value achieved upon the first charging of the device at a full voltage application.

In any of the above aspects, the cathodic material may be a viologen, a low-dimerizing viologen or a non-dimerizing viologen. The term low-dimerizing viologen is applied to some viologens that show dimerization characteristics to a lesser extent that dimerizing viologens. Illustrative viologens include, but are not limited to, methyl viologen, octyl viologen, benzyl viologen, polymeric viologens, and the viologens described in U.S. Pat. Nos. 4,902,108; 6,188,505; 5,998,617; and 6,710,906. Other viologens may include those of Formula (I), (III), or (IV):

Formula (I)

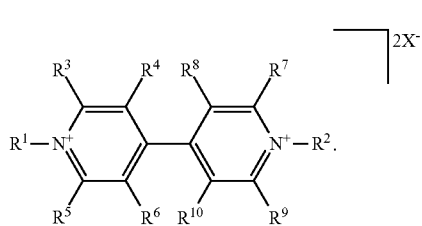

In Formula I, $R^1$ and $R^2$ are individually alkyl, siloxy alkyl, hydroxyalkyl, alkenyl, or aralkyl; $R^4$, $R^6$, $R^8$, and $R^{10}$ are individually H, OH, F, Cl, Br, I, CN, $NO_2$, alkyl, alkoxy, or aryl; $R^3$, $R^5$, $R^7$, and $R^9$ are individually H, OH, F, Cl, Br, I, CN, $NO_2$, alkyl, alkoxy, or aryl, and X is an anion.

However, Formula (I) may be subject to the proviso that $R^3$ and $R^5$, or $R^7$ and $R^9$, or $R^3$, $R^5$, $R^7$, and $R^9$ are individually secondary alkyl, tertiary alkyl, or aryl.

Formula (III)

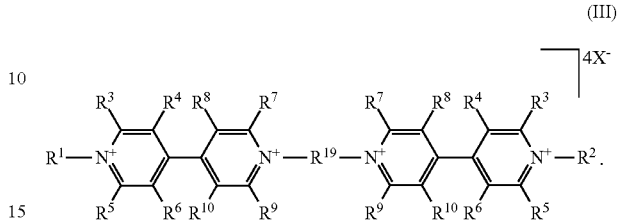

In Formula (III), $R^1$ and $R^2$ are individually alkyl, siloxyalkyl, hydroxyalkyl, alkenyl, or aralkyl; $R^4$, $R^6$, $R^8$, $R^{10}$ are individually H, OH, F, Cl, Br, I, CN, $NO_2$, alkyl, alkoxy, or aryl; $R^3$, $R^5$, $R^7$, and $R^9$ are individually H, OH, F, Cl, Br, I, CN, $NO_2$, alkyl, alkoxy or aryl; $R^{19}$ is $(CH_2)_{n'}$ or arylene, and n' is from 1 to 12; X is an anion; and wherein $R^3$ and $R^5$, or $R^7$ and $R^9$ are individually secondary alkyl, tertiary alkyl, or aryl.

Formula (IV)

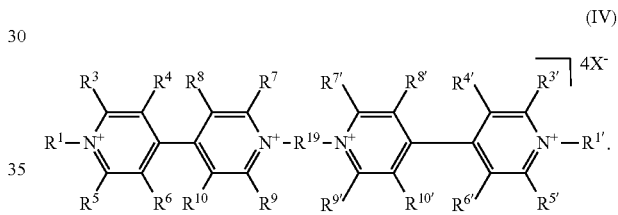

In Formula (IV), $R^1$ and $R^{1'}$ are individually alkyl, siloxyalkyl, hydroxyalkyl, alkenyl, or aralkyl; $R^4$, $R^6$, $R^8$, $R^{10}$, $R^{4'}$, $R^{6'}$, $R^{8'}$, and $R^{10'}$ are individually H, OH, F, Cl, Br, I, CN, $NO_2$, alkyl, alkoxy, or aryl; $R^7$, $R^9$, $R^{7'}$, and $R^{9'}$ are individually H, OH, F, Cl, Br, I, CN, $NO_2$, alkyl, alkoxy, or aryl; $R^{19}$ is $(CH_2)n'$ or arylene, and n' is from 1 to 12; X is an anion; and either $R^3$, $R^5$, $R^{3'}$, and $R^{5'}$ are individually secondary alkyl, tertiary alkyl, or aryl; or $R^7$, $R^9$, $R^{7'}$, and $R^{9'}$ are individually secondary alkyl, tertiary alkyl, or aryl. In some embodiments, for the low-dimerizing or non-dimerizing electrochromic compound represented by Formula (IV), $R^{19}$ is $(CH_2)n'$ or arylene, and n' is from 1 to 12. For any of the viologens described, the counterion (anion) may be any of a halide, a borate, a fluoroborate, a tetraaryl borate, a hexafluoro metal or metalloid, a sulfate, a sulfonate, a sulfonamide, a carboxylate, a perchlorate, a tetrachloroferrate, or the like, or mixtures of any two or more thereof. Illustrative counterions/anions include, but are not limited to: $F^-$, $Cl^-$, $Br^-$, $I^-$, $BF_4^-$, $PF_6^-$, $SbF_6^-$, $AsF_6^-$, $ClO_4^-$, $SO_3CF_3^-$, $N(CF_3SO_2)_2^-$, $C(CF_3SO_2)_3^-$, $N(SO_2C_2F_5)^-$, or $BAr_4^-$, wherein Ar is a aryl or a fluorinated aryl or a bis(trifluoromethyl) aryl group. In some embodiments, X is a tetrafluoroborate or a bis(trifluoromethylsulfonyl) imide anion.

In any of the above aspects, the anodic material may be a phenazine, a phenothiazine, a triphenodithiazine, a carbazole, a indolocarbazole, a biscarbazole, or a ferrocene covalently attached to, or confined within, the second polymer matrix, the second polymer matrix configured to prevent or minimize substantial diffusion of the anodic material in the activated state. As with the viologen, the anodic material may be sequestered within the polymer matrix by being physically trapped within, or the anodic material may be functionalized such that it is amenable to being polymerized or reacted with the polymer to be covalently bonded to the polymer.

In some embodiments, the anodic material may be a compound represented by:

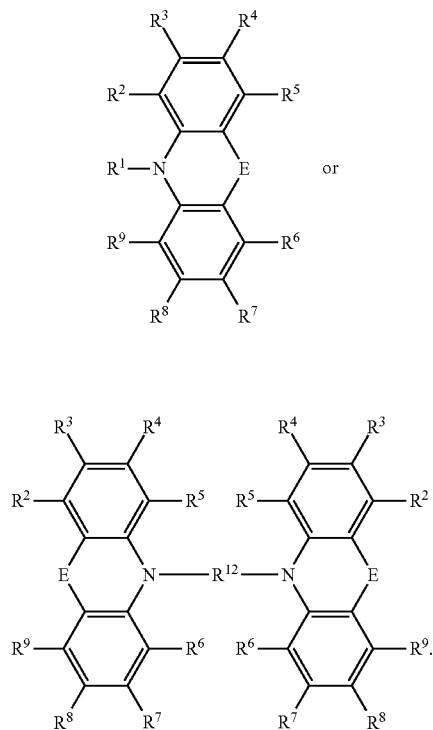

In the above formula, E is S or $NR^{10}$; $R^1$ and $R^{10}$ are individually an alkyl group interrupted by at least one ammonium group; each $R^2$-$R^9$ are individually H, F, Cl, Br, I, CN, $OR^{11}$, $SR^{11}$, $NO_2$, alkyl, alkoxy aryl, amino, or any two adjacent groups of $R^2$-$R^9$ may join to form a monocyclic, polycyclic, or heterocyclic group; each $R^{11}$ is individually H or alkyl; and $R^{12}$ is an alkylene group. In some embodiments, E is $NR^{10}$ and $R^2$-$R^9$ are H or $OR^{11}$. In other embodiments, E is S and $R^7$ and $R^8$ join to form a heterocyclic group.

The anodic material may be a compound represented by:

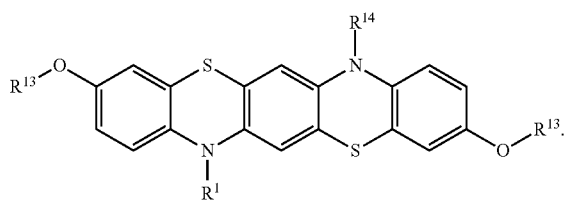

In the above formula, $R^{14}$ is an alkyl group interrupted by at least one ammonium group. In any of the compounds described above, $R^1$, $R^{10}$, and $R^{14}$ may be represented by:

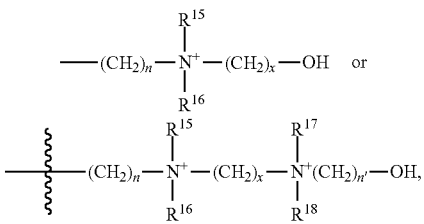

where $R^{15}$-$R^{18}$ are individually H or alkyl; n is 1, 2, 3, 4, 5, 6, 7, 8, 9, 10, 11, or 12; n' is 1, 2, 3, 4, 5, 6, 7, 8, 9, 10, 11, or 12; and x is 1, 2, 3, 4, 5, 6, 7, 8, 9, 10, 11, or 12. In some embodiments, n is 4, x is 2, and n' is 11.

Further examples of anodic and cathodic materials may be found in U.S. Pat. Nos. 4,902,108; 5,294,376; 5,998,617; 6,193,912; and 8,228,590.

Where the cathodic or anodic materials are sequestered within a polymer matrix, the polymer matrix may be solid polymer or gel polymer. For example, the polymer may be an acrylate-based polymer that is dissolved in a solvent which incorporates the anodic or cathodic material. This solution is then coated on the conductive surface of a substrate, where the solvent is then removed. The resultant film is an acrylate film that may be hard or tacky to the touch. Or, the polymer film maybe a gel that contains solvent as well as the anodic or cathode material. In addition, the polymer film maybe subsequently cross-linked for increased mechanical stability. Other possible polymer matrix systems that could be used to sequester an anodic and cathodic materials: polyacrylate, polymethacrylates, polyethers, polyesters, polycarbonates and polyurethanes, polysiloxanes, polysilanes, polyacrylonitriles, polystyrenes, polymethacrylonitriles, polyamides, polyimides, polyvinylidenehalides, and co-polymers or combinations of any two or more thereof. Further examples of polymer matrix materials used in electrochromic devices can be found in U.S. Pat. Nos. 6,635,194 and 5,940,201.

As noted above, the anodic or cathodic materials may also be part of the polymeric matrix with the anodic or cathodic material being covalently bound to the polymer. This may be accomplished with the presence of a functional group on the anodic or cathodic material that is reacted with the polymer or monomers that make up the polymer. For example, where the anodic or cathodic materials contain a hydroxyl group, the anodic or cathodic material may be bound into a polymer matrix via a condensation reaction or react with isocyanate functionality to form a polyurethane-based polymer matrix. Amines may also react with isocyanate functionalities to form urea and biuret linkages. It can be also anticipated that other cross-linked polymeric matrix can be formed using a multifunctional epoxy or polymers in combination with a curing agent like an amine, alcohol or anhydride or through base or acid catalyzed homopolymerization.

Illustrative materials that may be used as the first and second polymer matrix materials include, but are not limited to, polymethylmethacrylate, polypropylene methacrylate, polystyrene, polyurethanes, polyethers, polyesters, polycarbonates, polysiloxanes, polysilanes, polyacrylonitriles, polymethacrylonitriles, polyamides, polyimides, polyvinylidenehalides, and co-polymer and combinations of thereof. Further examples of polymer matrix materials can be found in U.S. Pat. Nos. 6,635,194 and 5,940,201.

The energy storage devices may exhibit an open circuit voltage of 0.2 V to 1.2 V. In some embodiments, the energy storage devices may exhibit an open circuit voltage of 0.6 V to 0.8 V. The energy storage devices may exhibit a discharge current of 100 μA to 1000 μA.

Where the devices include an optional electrolyte, the electrolyte may include a solvent and a salt. The salt may be a metal salt or an ammonium salt. Illustrative solvents for use in the electrolyte may include, but are not limited to, 3-methylsulfolane, dimethyl sulfoxide, dimethyl fornamide, tetraglyme and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, gamma-butyrolactone, and gamma-valerolactone; propylene carbonate (PC), ethylene carbonate; and homogenous mixtures of the same. While specific solvents have been disclosed as being associated with the electrolyte, numerous other solvents that would be known to those having ordinary skill in the art having the present disclosure before them are likewise contemplated for use. Illustrative salts include, but are not limited to, metal or ammonium salts, such as but not limited to $Li^+$, $Na^+$, $K^+$, $NR'_4{}^+$, where each R' is individually H, alkyl, or cycloalkyl, of the following anions $F^-$, $Cl^-$, $Br^-$, $I^-$, $BF_4{}^-$, $PF_6{}^-$, $SbF_6{}^-$, $AsF_6{}^-$, $ClO_4{}^-$, $SO_3CF_3{}^-$, $N(CF_3SO_2)_2{}^-$, $C(CF_3SO_2)_3{}^-$, $N(SO_2C_2F_5)^-$, $Al(OC(CF_3)_3)_4{}^-$, or $BAr_4{}^-$, wherein Ar is an aryl or fluorinated aryl group such as, but not limited to, $C_6H_5$, $3,5$-$(CF_3)_2C_6H_3]_4$, or $C_6F_5$.

With regard to the substrates and conductive coatings on the substrates, those typically used in solution-based electrochromic devices may be used. For example, the one or both substrates may be glass, metal, plastic, or ceramic. The conductive coating on one or more of the substrates may be transparent or opaque depending upon the intended use of the device. For example, where the device is a window, both coatings should be substantially transparent, and where the device is a mirror at least one coating is transparent. Illustrative, transparent conductive materials include, but are not limited to, fluorine doped tin oxide (FTO), indium/tin oxide (ITO), doped zinc oxide, indium zinc oxide, metal oxide/ Ag/metal oxide, silver nano-wire coatings, carbon nanotubes, graphene coatings, wire grids, conductive polymers such as, but not limited to, poly(3,4-ethylenedioxythiophene) (PEDOT). Non-transparent conductive coatings include metal coatings such as rhodium, chromium, nickel, silver, gold, and other metals, or mixtures of any two or more thereof.

The present invention, thus generally described, will be understood more readily by reference to the following examples, which are provided by way of illustration and are not intended to be limiting of the present invention.

EXAMPLES

Example 1

An indium tin oxide (ITO) coated piece of 3"×3" glass (2.2 mm thickness) was coated with a mixture made by dissolving 0.69 grams of bis (11-hydroxyundecyl) viologen bis[bistrifluoromethanesulfonyl imide] (NTf) and 0.23 grams of HDT (aliphatic polyisocyanate available under the tradename BASONAT® HI from BASF) in a 7.0 gram solution of 9 wt % PMA (poly(methylacrylate)) in propylene carbonate (PC), plus 110 mircroliters of a 1% solution of dibutyltin diacetate (DBTDA) catalyst in PC thereby forming a first film. This coating was made using a #10 Mayer rod to control thickness. A second piece of 3"×3" glass (2.2 mm thickness) was coated with a solution made by dissolving 0.830 grams of triphenodithiazine diol from example 2 and 0.135 grams of HDT in 9 wt % PMA and 110 miroliters of DBTDA in PC thereby forming a second film. This film was also made with a #10 Mayer rod. The films were allowed to cure under a nitrogen atmosphere overnight in an oven (70° C.). The first and second films, on their respective glass substrates, were positioned in a spaced-apart relationship facing each other and an epoxy seal was placed around the perimeter and cured to form a cell leaving offsets for attachment of electrical contacts. The distance between the two substrates was about 500 microns. The resulting cell was filled with a solution of 0.2 M tetraethylammonium tetrafluoroborate ($TEABF_4$) and a cross-linkable polymer matrix precursor in PC to form a polymeric electrolyte. Illustrative cross-linkable polymer matrices are described in U.S. Pat. No. 6,635,194. After filling and plugging of the cell, the cell was placed in an oven overnight to cure the polymeric electrolyte.

Example 2. Synthesis of an Bis-Hydroxy Tetra-Quaternary Ammonium Triphenodithiazine Tetra (Bistrifluoromethane Sulfonylimide) or [$N^1,N^{1'}$-((3, 10-dimethoxybenzo[5,6][1,4]thiazino[2,3-b] phenothiazine-7,14-diyl)bis(butane-4,1-diyl))bis($N^2$-(2-hydroxy-2λ,11λ-undecyl)-$N^1,N^1,N^2,N^2$-tetramethylethane-1,2-diaminium)]

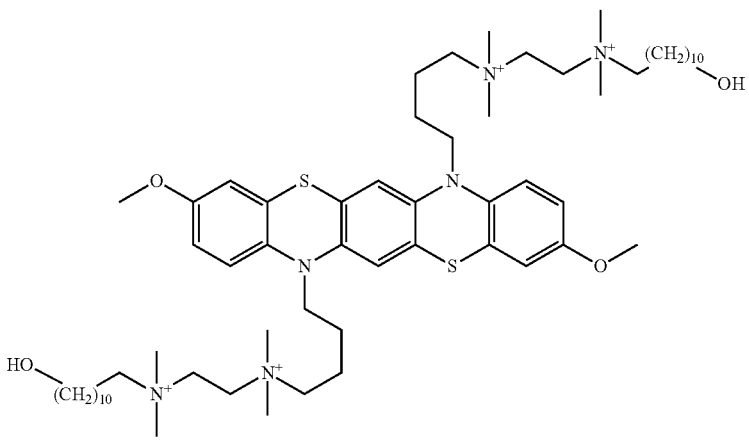

Step 1. A solution of 3,10-dimethoxy-7,14-(4-bromobutyl) triphenodithiazine (30 g; prepared according to procedure in U.S. Pat. No. 6,710,906), and (N,N-dimethylaminoethylene)-dimethyl-11-hydroxyundecyl ammonium bis(trifluoromethanesulfonimide) (209 g, Example 5) in a solvent mixture of acetonitrile (300 ml) and 2-butanone (840 ml) was heated at 65° C. for 17 days. The product was isolated by filtration.

Step 2. Conversion of the bromide salt to the bistrifluoromethanesulfonyl imide salt. 27 g of the solid from Step 1 was dissolved in hot water (400 ml) and ethanol (500 ml). The resulting solution was then heated to 80° C. for 2.5 hours and hot-filtered. 122 g of lithium bis(trifluoromethane)sulfonyl imide (LiNTf) was then dissolved in 122 ml water. The LiNTf solution was the added to the triphenodithiazine solution, and heating was continued for 1.5 hours at 50° C. After cooling to room temperature, 400 ml water was added, and the product oiled out from solution. The filtrate was decanted. A second metathesis was done with 40 g LiNTf in 100 ml water. The product oiled out, isolated and was dissolved in 4-methylpentanone (500 ml), followed by an extraction with 3×300 ml deionized water. The combined organic fractions were combined, dried over MgSO$_4$, filtered, and the solvent was removed under reduced pressure to provide 45 g of the desired product.

Example 3. Synthesis of 1,1'-di(6-bromohexanoyl)ferrocene

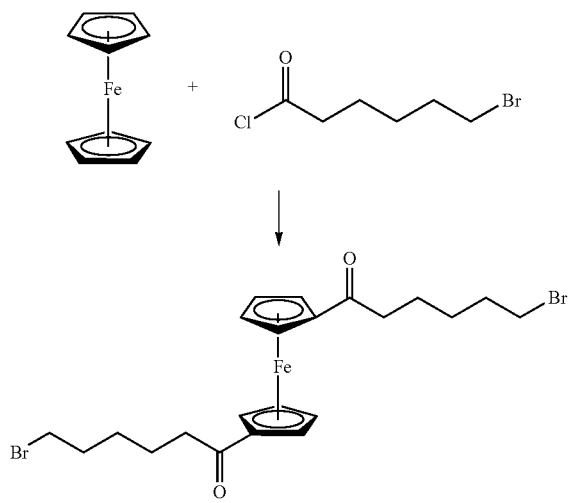

A 3-neck, round bottom flask equipped with an overhead stirrer, addition funnel, and nitrogen inlet at room temperature was charged with ferrocene (50 g, 0.27 mole) in 400 ml of dry dichloroethane. To the addition funnel was added a solution of AlCl$_3$ (72 g, 0.54 mole) and 6-bromohexanoyl chloride (116 g, 0.54 mole) in 250 ml of dry dichloroethane. The solution in the addition funnel was then slowly added to the ferrocene to form a purple solution that was stirred overnight.

The reaction was quenched by pouring on ice to form 2 layers, which were then separated to isolate the organic fraction. The organic fraction was extracted three times with 150 ml of water. After drying of the organic fraction with MgSO$_4$, the solution was filtered, the solvent removed, and the product recovered in 98% yield.

Example 4. Synthesis of 1,1'-di(6-bromohexyl)ferrocene

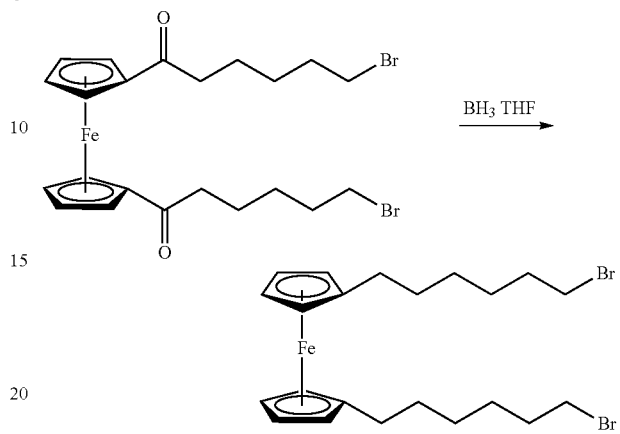

A 3-neck, round bottom flask equipped with an overhead stirrer, addition funnel, and nitrogen inlet at room temperature was charged with 1,1'-di(6-bromohexanoyl)ferrocene (20.8 g, 38.5 mmol, example 3) in 100 ml of THF at 0° C. From the addition funnel, a solution of borane tetrahydrofuran complex solution (1 M, 100 mL) was added to the 1,1'-di(6-bromohexanoyl)ferrocene. The mixture was stirred while warming to room temperature, followed by continued stirring overnight. The reaction mixture was then heated at 70° C. for 3 to 4 hours and cooled to room temperature. After quenching with ethanol, all solvents were removed by evaporation. The residue was then dissolved in 150 ml of diethyl ether and the solution washed with 75 ml of an aqueous HCl solution (1N), followed by neutralization with NaHCO$_3$ solution (1N). The diethyl ether solution was washed with deionized water (100 ml) until neutralization. After drying over MgSO$_4$ and solvent was removed, the product was isolated in 95% yield.

Example 5. Synthesis of (N,N'-dimethylaminoethylene)-dimethyl-11-hydroxyundecyl Ammonium Bistrifluoromethanesulfonylimide

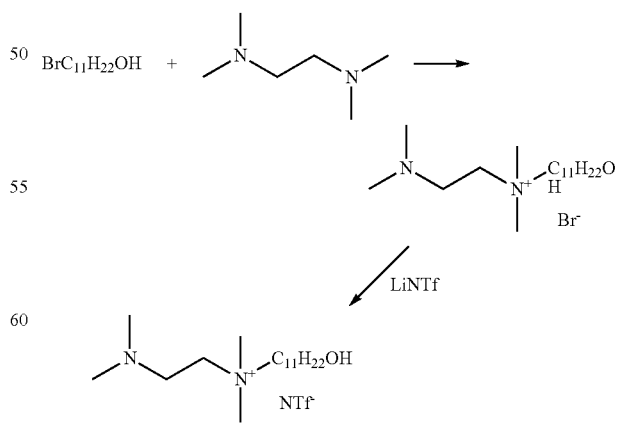

A mixture of freshly distilled tetramethylethylenediamine (75 g) and 11-bromoundecanol (25 g) in 150 ml of acetone was stirred at room temperature overnight. A white solid formed during the reaction and was collected by filtration and washed with acetone and ethyl ether. After drying, the solid obtained as the bromide salt was pure (33 g, 94% yield). The bis(trifluoromethane)sulfonimide) salt was obtained by metathesis of bromide salt with lithium bis(trifluoromethane)sulfonimide in water. The desired product was extracted with ethyl acetate and dried with MgSO$_4$ for isolation.

Example 6

Synthesis of 1,1'-bis(N-(11-hydroxyundecanyl)-N'-hexyl-N,N,N',N'-tetramethylethylenediammonium) ferrocene tetra Example 7A Synthesis of N,N'-bis(11-hydroxyhexyl)-4,4'-bypyridinium di(bis(trifluoromethane)sulfonamide. Conducted in a manner analogous to the preparation of N,N'-bis(11-hydroxyundecyl)-4,4'-bipyridinium di(bis(trifluoromethane) sulfonamide (example 7), but using bromohexanol instead of 11-bromoundecanol.

Example 8. Synthesis of 2-methyl-4-hydroxy phenyl viologen

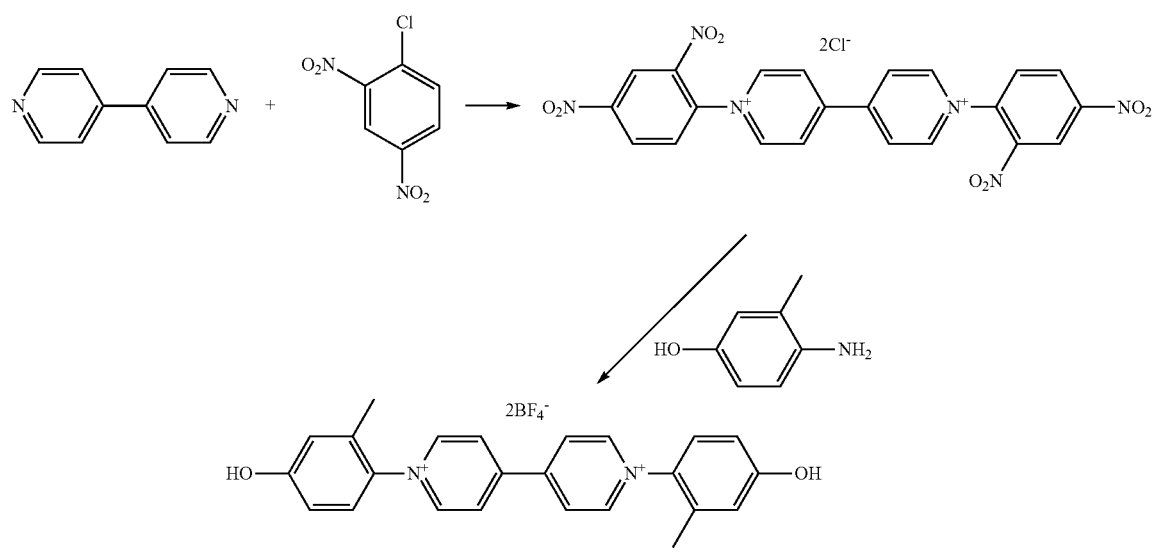

(bis(trifluoromethane)sulfonimide). A mixture of 1,1'-di(6-bromohexyl)ferrocene (17 g, 0.033 mol) and N,N,N',N'-tetramethylethylenediamine-N-(11-hydroxyundecanyl) ammonium bis(trifluoromethane)sulfonimide (74 g, 0.13 mol) in a 1:1 mixture of methylethylketone (MEK) and acetonitrile was refluxed overnight, before cooling to room temperature. A yellow solid was collected by filtration. The solid was recrystallized from hot ethanol to yield 51% of pure bromide product. The desired product was obtained by metathesis of the bromide salt with lithium bis(trifluoromethane)sulfonimide in water.

Example 7

Synthesis of N,N-bis(11-hydroxyundecyl)-4,4'-bipyridinium di(bis(trifluoromethane)sulfonamide. A mixture of 4,4'-bipyridine (25 g, 0.16 mol) and 11-bromoundecanol (100 g, 0.4 mol) in acetonitrile (800 ml) and 4-methyl-2-pentanone (200 ml) was refluxed for 24 hours. On cooling, a yellow solid precipitated, and was collected by filtration. The bromide solid was obtained by recrystallization from hot ethanol and water, and was isolated (67 g, 47% yield). The NTf salt was obtained by metathesis of the bromide salt with LiNTf in water.

Step 1. To a 2 L flask was added 4,4-dipyridyl (31.2 g), 1-chloro-2,4-dinitrobenzene (162 g), and acetonitrile (1000 ml). The reaction mixture was heated at reflux for 8 days. After cooling to room temperature, a light yellow solid was filtered and dried to provide 2,4-dinitro phenyl viologen dichloride (43 g; 44% yield).

Step 2. To a 250 ml flask was added 2,4-dinitrophenyl viologen dichloride (5 g), 4-amino metacresol (3.2 g), dimethyl formamide (25 ml), and water (25 ml). The reaction mixture was heated to 70° C. for 16 hours. After cooling to room temperature the reaction mixture was transferred to acetone (500 ml), and cooled at 5° C. for 2 hours. The solid product as the chloride salt was isolated by filtration (2.98 g; 67% yield).

The chloride salt of the desired product was then converted to the tetrafluoroborate salt by dissolution in methanol (50 ml), water (10 ml), and a 4 M solution of sodium tetrafluoroborate (30 ml). The solution was then heated to 60° C. for one hour before cooling to room temperature. The product (2.38 g; 54% yield) was collected by filtration and washed with water.

Example 9. Synthesis of 3-Hydroxyphenyl Viologen

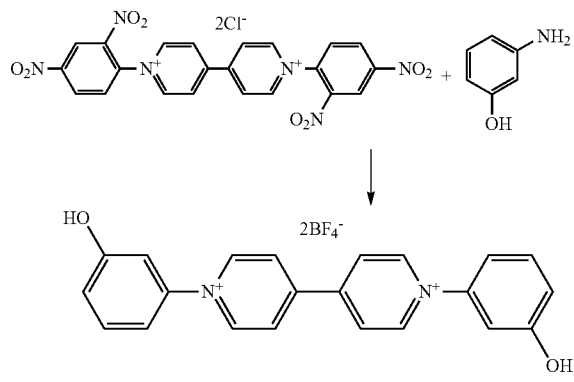

To a 500 ml flask was added 2,4-dinitro phenyl viologen (20 g; Example 8), 3-aminophenol (12 g), dimethyl formamide (170 ml), and water (20 ml). The reaction mixture was heated to 70° C. for 48 hours. After cooling to room temperature the reaction mixture was transferred to acetone (700 ml), and cooled at 5° C. for 2 hours. The solid product was isolated by filtration (13 g; 78% yield). The chloride salt of the desired product was converted to the tetrafluoroborate salt by dissolving in methanol (50 ml), water (100 ml), and a 4 M solution of sodium tetrafluoroborate (50 ml). The solution was heated to 60° C. for one hour and then cooled to room temperature. The product was filtered and washed with water to give light yellow desired product.

A second metathesis was done on the light yellow product by dissolving it in methanol (50 ml), acetonitrile (25 ml), and water (100 ml), a 4 M solution of sodium tetrafluoroborate (50 ml). The solution was heated to 60° C. for one hour and then cooled to room temperature. The product was filtered and washed with water to give a light yellow desired product (8.7 g; 52% yield).

Example 10

Device made in example 1 was evaluated as a battery. After approximately 2000 charge/discharge cycles the cell was the powered and held at open circuit. After a few minutes the open circuit voltage was again measured and found to have maintained a value of 0.7 V. The discharge current was 800 µA.

Example 11

Preparation of a battery. An ITO-coated piece of 3"×3" glass (2.2 mm thick) was coated with a solution made with 0.167 g of the viologen of Example 8, 0.016 g of the viologen of Examples 9, 0.14 g HDT and 110 micro-liters of a 1% DBTDA dissolved into 9 wt % PMA PC. A second film was made by coating another 3"×3" ITO-coated piece of glass (2.2 mm thick) with a solution of 0.78 g of the ferrocene diol with 0.135 g HDT and 110 micro-liters DBTDA into 7 g of a 9 wt % PMA solution in PC. The films were also allowed to cure overnight in a 70° C. oven. The two films we positioned in a spaced-apart relationship facing each other and a seal was cured around the perimeter of the formed cell leaving offsets to contact each electrode. The resulting cell was filled with a solution of TEABF$_4$ and a cross-linkable polymer matrix precursor in PC. The electrolyte layer was allowed to crosslink overnight in an oven (60° C.). After approximately 400 charge/discharge cycles, the cell was powered and an open circuit voltage of 0.496 V was measured. The device had a discharge current of 200 tA.

Example 12

Preparation of an electrochromic battery with a membrane. A battery including an anion exchange membrane as a separator was made by first making two gelled fluids and sandwiching a membrane between them. A first gel was prepared by mixing and degassing under nitrogen N,N'-bis[3-(triethyl)ammonium)propyl]-N,N'-dihydrophenazine bis(tetrafluoroborate) (0.106 g, synthetic procedure can be found in U.S. Pat. No. 6,710,906), tetraethylammonium tetrafluoroborate (0.106 g), 212-250 µm glass beads (0.310 g), and PC (5.37 g). Fumed silica (0.360 g; Aerosil 300) was mixed into the solution thereby forming a thickened gelled fluid.

A second gel was prepared by mixing and degassing under nitrogen gas dioctylviologen bis(tetrafluoroborate) (0.143 g), tetraethylammonium tetrafluoroborate (0.109 g), 212-250 micron diameter glass beads (0.300 g), and PC (5.46 grams). Fumed silica (0.360 g) was mixed into the solution forming a thickened gelled fluid.

A splat cell battery was formed by taking two sheets of ITO-coated glass that were equipped with bus-bars for electrical contact. The sheets of ITO were both 3×3 inches in size and 2.2 mm thick. The splat cell was made by first taking one sheet of ITO-coated glass (ITO up) and placing 0.106 grams of the first gel in the center of the glass. Then, a 3×3 cm anion exchange membrane was placed on top of the gel. This anion exchange membrane was from Membranes International Inc., in Ringwood N.J., USA, membrane AMI-7001S and is about 0.450 mm thick. The membrane was preconditioned in a solution of 0.100 M tetraethylammonium tetrafluoroborate in propylene carbonate for an hour. Then, 0.180 grams of the second gel is placed on top of the membrane, followed by the second sheet of ITO coated glass (ITO down). Glass spacers, 850-900 microns in diameter were affixed in the four corners of the splat cell to assist in defining the cell spacing. Finally, two binder clips were used to hold the splat cell together. The two gelled solutions were completely separated by the membrane.

The splat cell was held in a nitrogen atmosphere for an hour before charging for 10 minutes at 1.25 volts. Within the first minute of charging, the top gel (second gel) becomes very dark blue, which is an indication of reduction of the viologen. This splat cell is then left in open circuit for 10 minutes while still under a nitrogen atmosphere. At the end of the 10 minutes, the measured voltage was 0.680 V and the discharge current was 410 tA.

Example 12A

Example 12 was repeated. In this experiment, 0.128 grams of anodic gel and 0.103 grams of cathodic gel were used. The two gels were completely separated by the anionic exchange membrane. The splat cell was held in a nitrogen atmosphere for an hour before charging for 10 minutes at 1.25 volts. Like Example 12, within the first minute of charging, the top gel (cathodic gel) becomes very dark blue. The Splat cell is then left in open circuit for a 6 hours while still under a nitrogen atmosphere. At the end of the 6 hours, the measured voltage was 0.602 V and the discharge current was 200 μA. The device remained very dark blue in color.

Example 12B

Example 12 was repeated using a filter paper separator. In this experiment, 0.102 grams of anodic gel and 0.140 grams of cathodic gel were used. Unlike Example 12, the anionic exchange membrane was replaced by a 1½ inch square sheet cellulose filter paper. The paper material was Whatman filter paper, grade 1, supplied by GE Healthcare. The filter paper was preconditioned overnight in a solution of 0.100 M tetraethylammonium tetrafluoroborate in propylene carbonate.

The construction of the splat cell was the same as in Example 12 and the two gels were completely separated by the filter paper. The splat cell was held in a nitrogen atmosphere for an hour before charging for 10 minutes at 1.25 volts. Like Examples 12 and 12A, within the first minute of charging, the splat cell becomes very dark blue, and then allowed to stand at open circuit for 6 hours while under a nitrogen atmosphere. Within the first hour, the electrochromic splat cell started to clear and at the end of the 6 hours, the measured voltage was 0 mV and the splat cell was slightly green in color.

Without being bound by theory, it is believed that the open circuit voltage is determined by the oxidation potential of the anodic component and the reduction potential of the cathodic component. In some embodiments, the following pairs of anodic and cathodic materials may be employed:

| Anodic | Cathodic | ΔE (V) |
|---|---|---|
| 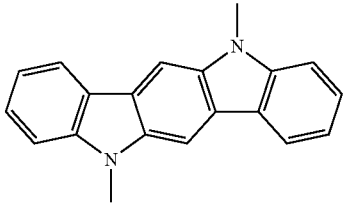 [SMILES: Cn1c2ccccc2c2cc3c(cc21)c1ccccc1n3C] | 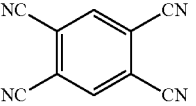 | 1.408 |

Example 13. Synthesis of bis-5,10-(4-(bromobutyl)-5,10-dihydrophenazine and a Butyl Bridged Bis(Phenazine)

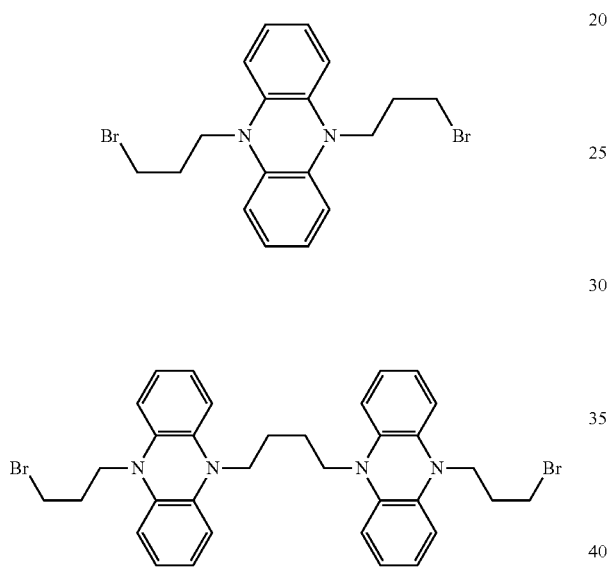

Phenazine (95.0 g), sodium dithionite (6.0 g), sodium carbonate (6.5 g), 1,4-dibromobutane, (100 ml), tributylmethyl ammonium chloride (2 ml), water (2 ml), and acetonitrile (100 ml) are combined in a 250 ml flask. The reaction mixture was heated to 80° C. for 24 hours. The reaction was then quenched with water (100 ml). Filtered the solid to give 7.7 g of mixture 60% desired and 40% butyl bridged bis(phenazine).

Example 14. Synthesis of a Hydroxy Quaternary Amine Phenazines

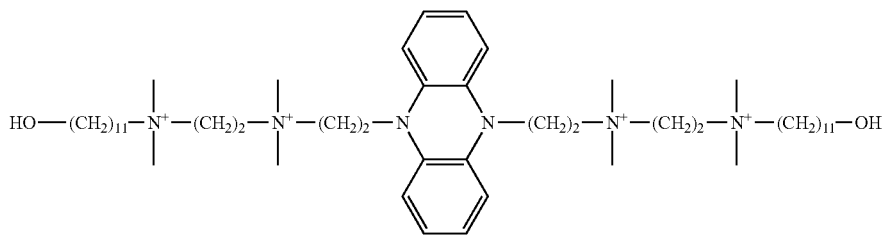

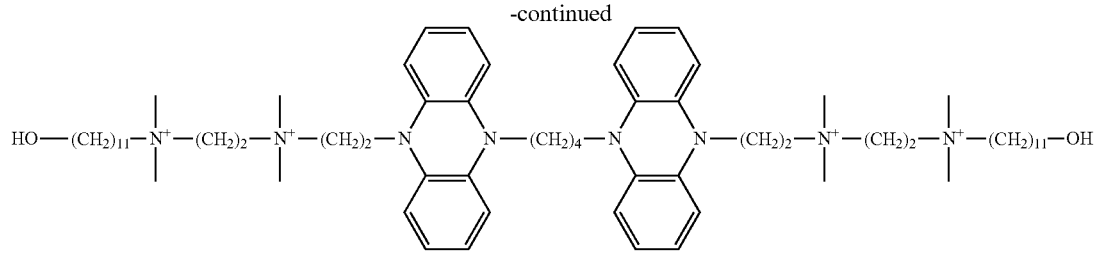

The mixture of bromobutyl phenazines from Example 13, plus (N,N-dimethylaminoethylene)-dimethyl-11-hydroxyundecyl ammonium bistrifluoromethanesulfonylimide (43 g, Example 5), acetonitrile (200 ml), and 2-butanone (50 ml) was added to a 250 ml flask and heated at 65° C. for 5 days. This reaction is then cooled and the product is filtered. The bromide salts were then dissolved in water (150 ml) and ethanol (100 ml) to form a bromide salt solution. In a separate flask, LiNTf (80 g) was dissolved in water (100 ml) and was then added to the bromide salt solution. The resultant mixture was then heated for one hour before cooling to room temperature. The product oiled out upon cooling. After decantation of the filtrate, the oily product was dissolved in 4-methyl pentanone (100 ml) and washed with 3×(100 ml) water. The organic layer was then dried and the solvent removed to yield 13.7 g of above compounds as the NTf salts.

Example 14 A. Synthesis of 3,10-t-butyl-7,14-bis(tri(2-hydroxyethyl)ammoniumbutylene) triphenodithiazine bis(trifluoromethane sulfonyl)imide

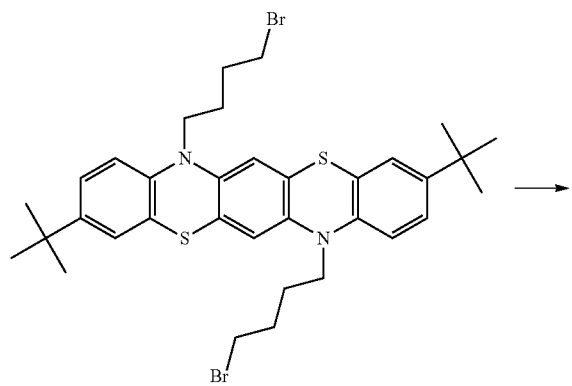

→

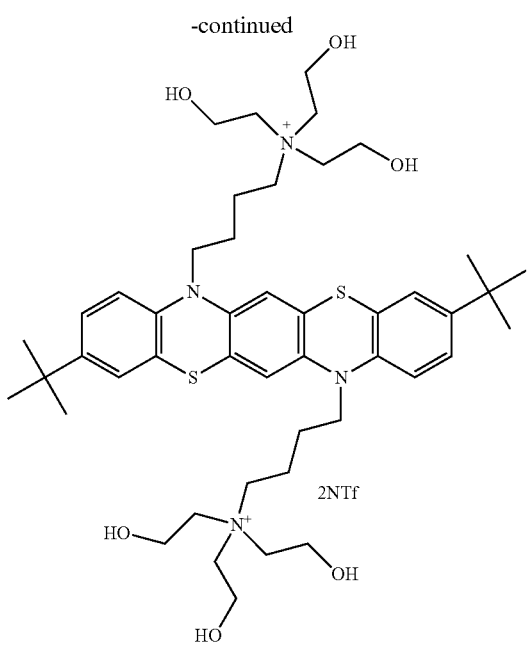

N,N-bromobutyl-p-t-butyl triphenodithiazine (10.0 g) and triethanol amine (34 g) were dissolved in acetonitrile (100 ml), and the mixture was refluxed for 72 hours. After the mixture was cooled to room temperature, it was diluted with 250 ml ether. The resulting bromide salt was filtered. The bromide salt was converted to the NTf salt by dissolving the bromide salt in MeCN (44 ml) and water (100 ml). To this solution added 40 g lithium bis(trifluoromethane sulfonyl)imide, dissolved in 60 ml water. The solution was heated at 50° C. for two hours and then cooled to 0-5° C. An oil formed and was decanted from the aqueous phase. The process was repeated twice, and 12.9 g of product was isolated.

N,N-bromobutyl-p-t-butyl triphenodithiazine (10.0 g, general synthetic procedure can be found in U.S. Pat. No. 6,710,906) and triethanol amine (34 g) were dissolved in acetonitrile (100 ml), and the mixture was refluxed for 72 hours. After the mixture was cooled to room temperature, it was diluted with 250 ml ether. The resulting bromide salt was filtered. The bromide salt was converted to the bis(trifluoromethane sulfonyl)imide salt by dissolving the bromide salt in MeCN (44 ml) and water (100 ml). To this solution added 403 g lithium bis(trifluoromethane sulfonyl)imide, dissolved in 60 ml water. The solution was heated at 50° C. for two hours and then cooled to 0-5° C. An oil formed and was decanted from the aqueous phase. The process was repeated once more, and 12.9 g of product was isolated.

Example 15

A first film was prepared from a solution containing 0.345 g bis(11-hydroxyundecyl) viologen (example 7), 0.0925 g HDT, 7.0 g 9 wt % PMA solution in PC with 110 micro-liters of a 1% DBTDA solution. The first film was cast from the solution on a 3"×3" indium tin oxide (ITO) coated piece of glass, 2.2 mm thick, and allowed to cure overnight in a 70° C. oven. A second film was made by coating another 3"×3" ITO coated piece of 2.2 mm glass with a solution containing 0.844 g of the phenazine diol mixture from Example 14, 0.1346 g HDT, and 110 micro-liters of a 1% DBTDA solution into 7 g of a 9 wt % PMA in PC. The second film was also allowed to cure overnight in a 70° C. oven. The two films we positioned in a spaced-apart relationship facing each other and a seal was cured around the perimeter of the formed cell leaving offsets to contact each electrode. The resulting cell was filled with a solution of TEABF$_4$ and a cross-linkable polymer matrix precursor in PC. The electrolyte layer was allowed to crosslink overnight in a 70° C. oven. The device exhibited a light transmission of 74% without an applied voltage. Applying 1.2 V to the device, the light transmission decreased to 10.3% and a darkening time of 46 seconds.

The same solutions was used to make films on 7"×7" ITO coated glass substrates. The two films were positioned in a spaced-apart relationship facing each other and a seal was cured around the perimeter of the formed cell leaving offsets to contact each electrode. The resulting cell was filled with a solution of TEABF$_4$ and a cross-linkable polymer matrix precursor in PC. The electrolyte layer was allowed to crosslink overnight in a 70° C. oven. The device had a light transmission of 79%. Application of 1.2 V to the device resulted in a light transmission of 5% and a darkening time of 46 sec. This shows that the dependence of transition time to device size is small.

To demonstrate the memory properties of the device, the device was colored to its low-end transmission of 4%, and then left at open circuit for 32 hours. The % T as a function of time at open circuit is shown in the figure.

Example 16

A device was made in the same manner as Example 1 using bis(11-hydroxyundecyl) viologen as the cathodic material and the phenazine compound from Example 14 as the anodic material. The device had a high end transmittance of 74% and after application of 1.2 V to the device for 3 minutes, a transmittance of 12% was achieved. After 4000 cycles the device had a transmission range of 71% to 14%. After 19,700 cycles the device had a transmission range of 73% to 18%.

Example 17

A device was made in the same manner as Example 1 using bis(11-hydroxyundecyl) viologen as the cathodic material and the ferrocene compound from Example 6 as the anodic material. The device had a high end transmittance of 80% and after applying 1.2 V to the ITO electrodes for 3 minutes the device had a transmittance of 12%. After 4000 cycles the device had a transmission range of 82% to 13%. After 19,700 cycles the device had a transmission range of 76% to 21%.

Example 18

The device from Example 1 had a high end transmittance of 83% and after applying 1.2 V to the ITO electrodes for 3 minutes the device had a transmittance of 9%. After 4000 cycles the device had a transmission range of 80% to 13%.

Example 19. Preparation of N-(4-methoxyphenyl) toluidine

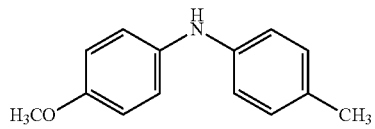

To flame dried flask charged p-toluidine (165 g), 4-bromoanisole (210 ml), sodium-t-butoxide (153 g), 1,1-(bisdiphenyl phosphine)ferrocene (1.8 g), tris(dibenzylidene acetone)dipalladium (1.02 g), and anhydrous toluene (1125 ml). The reaction mixture was heated to 80° C. After 48 hours of reflux, the reaction was quenched with 1 L water. The organic layer was separated, and the aqueous layer was extracted with toluene (300 ml). The combined organic layers were washed three times with water (300 ml), followed by drying with MgSO$_4$. The dried organic material was filtered and the solvent removed in vacuo, to provide an oil. After addition of hexane (1300 ml), the product solidified. The product was then recrystallized from toluene (400 ml) and hexane (1000 ml) to yield 166 g (51% yield).

Example 20. Preparation of 3-methyl-7-methoxy phenothiazine

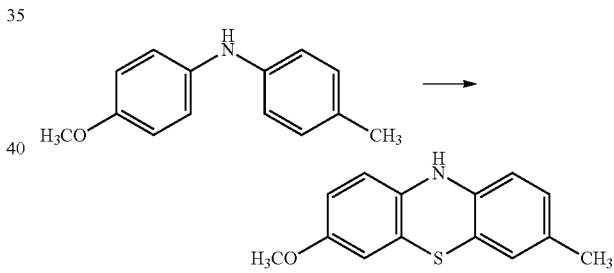

N-(4-methoxy phenyl)toluidine (50 g, example 19), sulfur (13.0 g), and iodine (1.5 g) were mixed and heated to 175° C. for 1.5 hours. After cooling to room temperature, tetrahydrofuran or THF (200 ml) and phenyl hydrazine (32 ml) were added. This mixture was heated to reflux for two hours, and cooled. The THF was removed in vacuo, followed by addition of ethanol (200 ml), and the mixture cooled in a refrigerator. Filtered the solid washed with ethanol and hexane to give 40 g (54% yield).

Example 21. Preparation of 3-methyl-7-methoxy-10-propanol phenothiazine

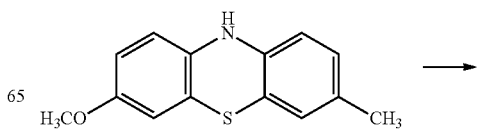

25

-continued

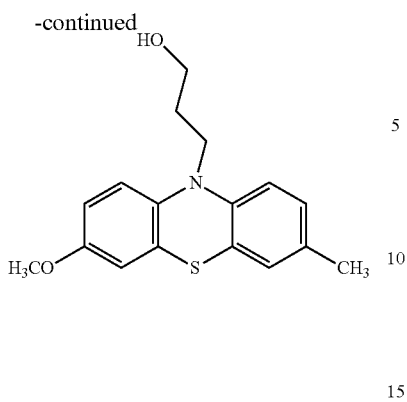

26

-continued

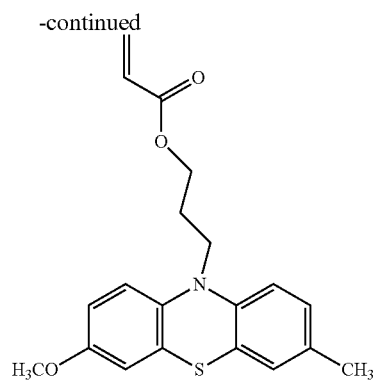

In a 1 L flask phenothiazine (16 g), sodium dithionite (13 g), sodium carbonate (17 g), methyl tributyl ammonium chloride (2 g), acetonitrile (400 ml), and water (2 ml), were heated at reflux for 72 hours. The reaction was then quenched with 250 ml water, and the organic layer separated. In a reaction flask, the organic material and triethyl amine (70 ml) were heated to reflux overnight. After cooling the mixture was filtered, and the solid rinsed with acetonitrile. The oily product was dissolved in ethyl acetate (100 ml) and washed with water (3×150 ml). The organic layer was then dried and stripped to give 13 g (65% yield).

Example 22. Preparation of 3-methyl-7-methoxy-10-propane acryl phenothiazine

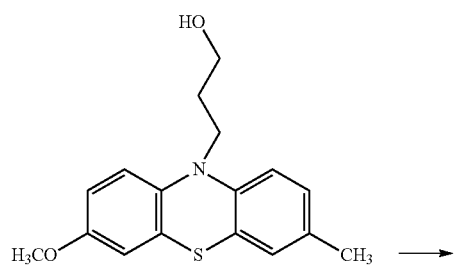

To a 250 ml flask was charged diisopropyl ethyl amine, propanol phenothiazine (13 g, example 21) and toluene (80 ml). Acryl chloride (5 ml) dissolved in toluene (15 ml) was then slowly added to the reaction mixture at 0° C. After stirring for 1.5 hours, 50 ml water was added, and the organic layer was separated and washed with an additional 50 ml water. The organic material was then dried with $MgSO_4$, filtered, and the solvent removed in vacuo. Hexane (200 ml) was added and the product oiled out. After decantation, any remaining solvent was removed in vacuo to give 8.0 g monomer product.

Example 23

Polymerization of phenothiazine monomer. Toluene (100 ml) was degassed with nitrogen for 3 hours, and then heated to 65° C. To a flame-dried flask was charged phenothiazine monomer (1.1 g, example 22), toluene (100 ml) and di(ethylene glycol)ethylene ether acrylate (1.16 g). The mixture was degassed with nitrogen for 10 minutes prior to heating to 65° C. Azobisisobutyronitrile or AIBN (0.075 g) was added, and the resulting mixture stirred at 65° C. for 24 hours before cooling to room temperature, then methanol is added (40 ml). After cooling, the product oiled out. The oil was dissolved in THF (10 ml), and methanol was added to precipitate the product. After solvent removed and drying, 1.05 g of polymer were obtained. GPC analysis showed a Mw of 21,650 g/mol and a Mn of 13,369 g/mol.

Example 24

Preparation of [1-(11-(2-methacryloyl-2'-carbamoyl)ethyl-N-undecanyl)-1'-methyl-4,4'-bipyridinium] [di(bis(trifluoromethane) sulfonimide)].

Step 1. A solution of methyl iodide (20 g) and 4,4'-bipyridine (10 g) in 100 ml of acetone was stirred at room temperature for overnight. A red solid formed during the reaction and was collected by filtration, rinsed with acetone and ethyl ether, and dried in air to obtain 19 g.

Step 2. To a solution of 20 g of ammonium 1 hexafluorophosphate in 50 ml of hot water (60° C.), a solution (50 ml) of 1-methyl-4,4'-bipyridinium iodide (19 g) in a mixed solvents (water and methanol 1:1 ratio) was slowly added. The mixture was stirred at 60° C. for 30 min and was cooled down to room temperature. A white solid was collected, rinsed with cold water and ether, and dried in air. Yield: 19 g, 95%.

Step 3. A reaction mixture of 13.5 g of 1-methyl-4,4'-bipyridinium hexafluorophosphate and 15 g of 1-bromo-11-undecanol in 100 ml of acetonitrile was refluxed for overnight. On cooling, a pale yellow material was collected, rinsed with cold acetonitrile and ether, and dried in air. Yield: 14 g; 50%. To a solution of 40 g of bis(trifluoromethane)sulfonimide lithium in 50 ml of hot water (60° C.), a solution (100 ml) of 14 g of the pale yellow solid in 100 ml of water was slowly added. The mixture was stirred at 60° C. overnight. On cooling, the product separated out from the solution as a liquid, and it was isolated. The liquid product was dissolved in 100 ml of 4-methyl-2-pentanone and dried with $MgSO_4$. After filtration, the solvent was removed under reduced pressure. Yield: 24 g; 99%.

Step 4. To a solution of 1-methyl-1'-undecanol-4,4'-bipyridinium di(bis(trifluoromethane) sulfonimide) (27.5 g) and 2-isocyanatoethylmethacrylate (5.0 g) in 80 ml of acetonitrile, 2 drops of dibutyltin diacetate was added. The mixture was stirred for 2 hours at room temperature. The product was precipitated by adding 300 ml of ethyl ether. The crude produce was dissolved in 50 ml of acetonitrile and was precipitated again with ethyl ether. The isolated liquid product was dried by vacuum. Yield: 30.8 g; 96.4%.

Example 24A

Preparation of viologen copolymer. To a solution of viologen monomer from Example 23 (4.76 g, 4.5 mmol) and methyl methacrylate (0.90 g, 9.0 mmol) in 3 ml of acetonitrile was made and 0.28 g of dimethyl 2,2'-azobis(2-methyl) propionate was added. The mixture was heated at 70° C. under $N_2$. After stirring for 24 hours, the reaction mixture was cooled to room temperature. The crude copolymer was isolated by adding 100 ml of ethyl acetate. The copolymer was purified from acetonitrile and ethyl acetate. Yield 2.5 g; 50%.

Example 25

Preparation of an electrochromic battery using a size-exclusion membrane as a separator was made by the same method highlighted in Example 12. A first gel was prepared by mixing and degassing under nitrogen the anodic phenothiazine polymer from Example 23 (0.0900 g), tetraethylammonium tetrafluoroborate (0.0856 g), 220-250 micro glass beads (0.126 g), and PC (3.04 g). Fumed silica (0.200 g; Aerosil 300) was mixed into the solution thereby forming a thickened gelled fluid.

A second gel, using a cathodic polymer, was prepared by mixing and degassing under nitrogen gas the polymer from Example 24A (0.200 g) Tetraethylammonium tetrafluoroborate (0.0675 g), 220-250 micron diameter glass beads (0.135 g), and PC (2.34 g). Fumed silica (0.158 g) was mixed into the solution forming a thickened gelled fluid.

The construction of the splat cell battery was the same as in Example 12. In this example, 0.106 g of the first gel containing the anodic polymer and 0.148 g of the second gel containing the cathodic gel were used. The separator for this example was an a size exclusion membrane cut out of a cellulose ester dialysis tube membrane from SpectrumLabs.com with a molecular weight cut-off (MWCO) of 100-500 daltons. The 3 cm×3 cm square membrane was preconditioned in a solution of 0.100 M tetraethylammonium tetrafluoroborate in propylene carbonate overnight. Glass spacers, 600-630 microns in diameter were affixed in the four corners of the splat cell to assist in defining the cell spacing.

The splat cell was held in a nitrogen atmosphere for an hour before charging for 10 minutes at 1.25 volts. Within the first minute of charging, the top gel (second gel) becomes very dark blue, which is an indication of reduction of the viologen. This splat cell is then left in open circuit for 10 minutes while still under a nitrogen atmosphere. At the end of the 10 minutes, the measured voltage was 0.680 V and the discharge current was 410 μA.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A energy storage device comprising:
   a cathodic material in an activated state; and
   an anodic material in an activated state;
   wherein:
      the energy storage device exhibits an open circuit voltage of about 0.2 V to about 1.4 V;
      the cathodic material is covalently attached to, or confined within, a first polymer matrix, the first polymer matrix configured to prevent or minimize substantial diffusion of the cathodic material; and
      the anodic material is a phenazine, a phenothiazine, a triphenodithiazine, a carbazole, a indolocarbazole, a biscarbazole, or a ferrocene covalently attached to, or confined within, a second polymer matrix, the second polymer matrix configured to prevent or minimize substantial diffusion of the anodic material.

2. The energy storage device of claim 1 that exhibits an open circuit voltage of about 0.6 V to about 0.8 V.

3. The energy storage device of claim 1 further comprising an electrolyte.

4. The energy storage device of claim 3, wherein the electrolyte comprises a solvent and salt is a metal salt or an ammonium salt.

5. The energy storage device of claim 1, wherein the cathodic material is a ferrocenium compound or 1,2,4,5-tetracyanobenzene.

6. The energy storage device of claim 1, wherein the cathodic material is 1,2,4,5-tetracyanobenzene.

7. The energy storage device of claim 1, wherein the cathodic material, the anodic material, or the cathodic and anodic materials are electrochromic.

8. The energy storage device of claim 1 which is a battery, capacitor, or supercapacitor.

9. The energy storage device of claim 1, wherein the anodic compound is represented by:

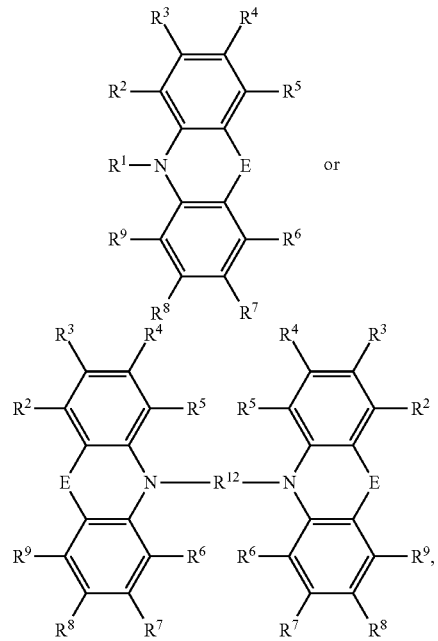

wherein:
   E is S or $NR^{10}$;
   $R^1$ and $R^{10}$ are individually an alkyl group interrupted by at least one ammonium group;
   $R^2$-$R^9$ are individually H, F, Cl, Br, I, CN, $OR^{11}$, $SR^{11}$, $NO_2$, alkyl, alkoxy, aryl, amino, or any two adjacent groups of $R^2$-$R^9$ may join to form a monocyclic, polycyclic, or heterocyclic group;
   each $R^{11}$ is individually H or alkyl; and
   $R^{12}$ is an alkylene group.

10. The energy storage device of claim 9, wherein E is $NR^{10}$ and $R^2$-$R^9$ are H or $OR^{11}$.

11. The energy storage device of claim 9, wherein the anodic compound is represented by:

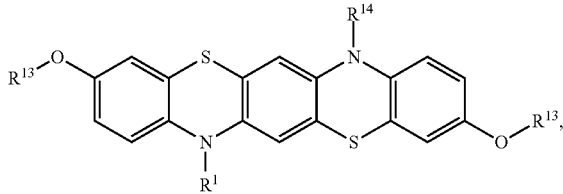

wherein:
   each $R^{13}$ is individually H or alkyl;
   $R^{14}$ is an alkyl group interrupted by at least one ammonium group.

12. The energy storage device of claim 11, wherein $R^1$ and $R^{14}$ are represented by:

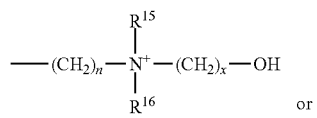

or

-continued

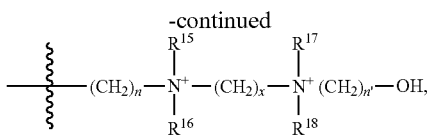

$R^{15}$-$R^{18}$ are individually H or alkyl;

n is 1, 2, 3, 4, 5, 6, 7, 8, 9, 10, 11, or 12;

n' is 1, 2, 3, 4, 5, 6, 7, 8, 9, 10, 11, or 12; and x is 1, 2, 3, 4, 5, 6, 7, 8, 9, 10, 11, or 12.

13. The energy storage device of claim 12, wherein n is 4, x is 2, and n' is 11.

14. A energy storage device comprising:
a first cell comprising an anodic material in an activated state;
a second cell comprising a cathodic material in an activated state;
a porous separator isolating the first cell from the second cell; and
wherein:
the cathodic material is a ferrocenium compound or 1,2,4,5-tetracyanobenzene; and
the anodic material is a phenazine, a phenothiazine, a triphenodithiazine, a carbazole, a indolocarbazole, a biscarbazole, or a ferrocene.

15. The energy storage device of claim 13 further comprising an electrolyte.

16. The energy storage device of claim 14, wherein the separator comprises an ion exchange membrane or a size-exclusion membrane.

17. The energy storage device of claim 14 which is a battery, capacitor, or supercapacitor.

18. The energy storage device of claim 14, wherein the cathodic material, the anodic material, or the cathodic and anodic materials are electrochromic.

* * * * *